United States Patent [19]
Woodward

[11] Patent Number: 5,846,762
[45] Date of Patent: Dec. 8, 1998

[54] STRUCTURALLY STABLE GEL BEAD CONTAINING ENTRAPPED ENZYME AND METHOD FOR MANUFACTURE THEREOF

[75] Inventor: Jonathan Woodward, Oak Ridge, Tenn.

[73] Assignee: Lockheed Martin Energy Research Systems, Inc., Oak Ridge, Tenn.

[21] Appl. No.: 489,304

[22] Filed: Jun. 9, 1995

Related U.S. Application Data

[63] Continuation of Ser. No. 936,162, Aug. 26, 1992, abandoned.

[51] Int. Cl.$^6$ ............................. C12P 1/00; C12N 11/04; C12N 11/06; B01J 13/20

[52] U.S. Cl. ............................. 435/41; 264/4.1; 264/4.3; 264/4.4; 427/213.3; 427/213.33; 427/213.35; 428/402.2; 428/402.24; 435/177; 435/178; 435/182

[58] Field of Search ........................ 264/4.1, 4.3, 4.4, 264/4; 427/213.3, 213.33, 213.35, 2.22; 428/402.2, 402.24; 435/177, 7.8, 41; 424/94.3; 530/817, 406; 536/3

[56] References Cited

U.S. PATENT DOCUMENTS

| | | | |
|---|---|---|---|
| 3,503,769 | 3/1970 | McDowell | 106/208 |
| 3,733,205 | 5/1973 | Shovers et al. | 427/213.35 X |
| 3,838,007 | 9/1974 | Van Velzen | 435/177 X |
| 4,092,219 | 5/1978 | Lin et al. | 435/177 X |
| 4,259,445 | 3/1981 | Glass et al. | 435/178 |
| 4,266,029 | 5/1981 | Branner-Jørgensen | 435/177 X |
| 4,572,897 | 2/1986 | Amotz et al. | 435/177 |
| 4,808,707 | 2/1989 | Daly et al. | 536/3 |
| 4,963,368 | 10/1990 | Antrim et al. | 424/498 |
| 4,978,647 | 12/1990 | Scott et al. | 502/7 |
| 4,995,985 | 2/1991 | Scott et al. | 210/679 |

FOREIGN PATENT DOCUMENTS

| | | | |
|---|---|---|---|
| 3076578 | 4/1991 | Japan | 435/177 |

OTHER PUBLICATIONS

Sterberg, D., Vijayakumar, P. and Reese, E. T., β–Glucosidase: microbial production and effect on enzymatic hydrolysis of cellulose, Can. J. Microbiol., vol. 23, pp. 139–147 (1977).

Bissett, F. and Sternberg, D., Immobilzation of Aspergillus Beta–Glucosidase on Chitosan, Applied and Environmental Microbiology, pp. 750–755 (Apr. 1978).

Sundstrom, D. W., Klei, Coughlin, R. W., Biederman, G. J. and Brouwer, C. A., Enzymatic Hydrolysis of Cellulose to Glucose Using Immobilized β–Glucosidase, Biotechnology and Bioengineering, vol. XXIII, pp. 473–485 (1981).

Woodward, J. and Wiseman, A., Fungal and other β–D–glucosidases–their properties and applications, Enzyme Microb. Technol., vol. 4, pp. 73–79 (Mar. 1982).

Woodward, J., and Wohlpart, D., Properties of Native and Immobilised Preparations of β–D–Glucosidase from *Aspergillus niger*, J. Chem. Tech. Biotechnol., vol. 32, pp. 547–552 (1982).

Lee, J. M. and Woodward, J., Properties and Application of Immobilized β–D–Glucosidase Coentrapped with Zymomonas Mobilis in Calcium Alginate, Biotechnology and Bioengineering, vol. XXV, pp. 2441–2451 (1983).

Bioproducts and Bioprocessess, Second Conferenced to Promote Japan/U.S. Joint Projects and Cooperation in Biotechnology, Lake Biwa, Japan, Sep. 27–30, 1986.

Novo's Handbook of Practical Biotechnology, Boyce, C.O.L. (Ed.), 2nd Edition, pp. 8–9, 63–99 (1986).

Woodward, J., and Clark, K. M., Hydrolysis of Cellobiose by Immobilized β–Glucosidase Entrapped in Maintenance-–Free Gel Spheres, Applied Biochemistry and Biotechnology, vol. 28/29, pp. 277–283 (1991.

Woodward, J. and Capps, K. M., "Cellobiose Hydrolysis by Glutaraldehyde–Treated B–Glucosidase Entrapped in Propylene Glycol Alginate/Bone Gelatin Spheres," Applied Biochemistry and Biotechnoloy, vol. 34/35 (1985), pp. 341–347.

Woodward, J., Koran, L. J., Hernandez, L. J., and Stephan, L. M., "Use of Immobilized B–Glucosidase in the Hydrolysis of Cellulose," ACS Symposium Series No. 533, 204th National Meeting of the American Chemical Society, Washington, D.C., Aug. 23–28, 1992, (1993), pp. 240–250.

*Primary Examiner*—Richard D. Lovering
*Attorney, Agent, or Firm*—Preston H. Smirman

[57] ABSTRACT

A structurally stable gel bead containing an entrapped enzyme and a method for its manufacture. The enzyme is covalently cross-linked to gelatin in the presence of glutaraldehyde prior to the formation of the gel bead, to prevent leakage of the enzyme. Propylene glycol alginate is then added to the mixture. Once the gel beads are formed, they are then soaked in glutaraldehyde, which imparts structural stability to the gel beads. This method can be used with many types of enzymes, such as proteases, carbohydrases, proteases, ligases, isomerases, oxidoreductases, and specialty enzymes. These and other enzymes can be immobilized in the gel beads and utilized in a number of enzymatic processes. Exogenously added ions are not required to maintain the structural stability of these gel beads.

3 Claims, 6 Drawing Sheets

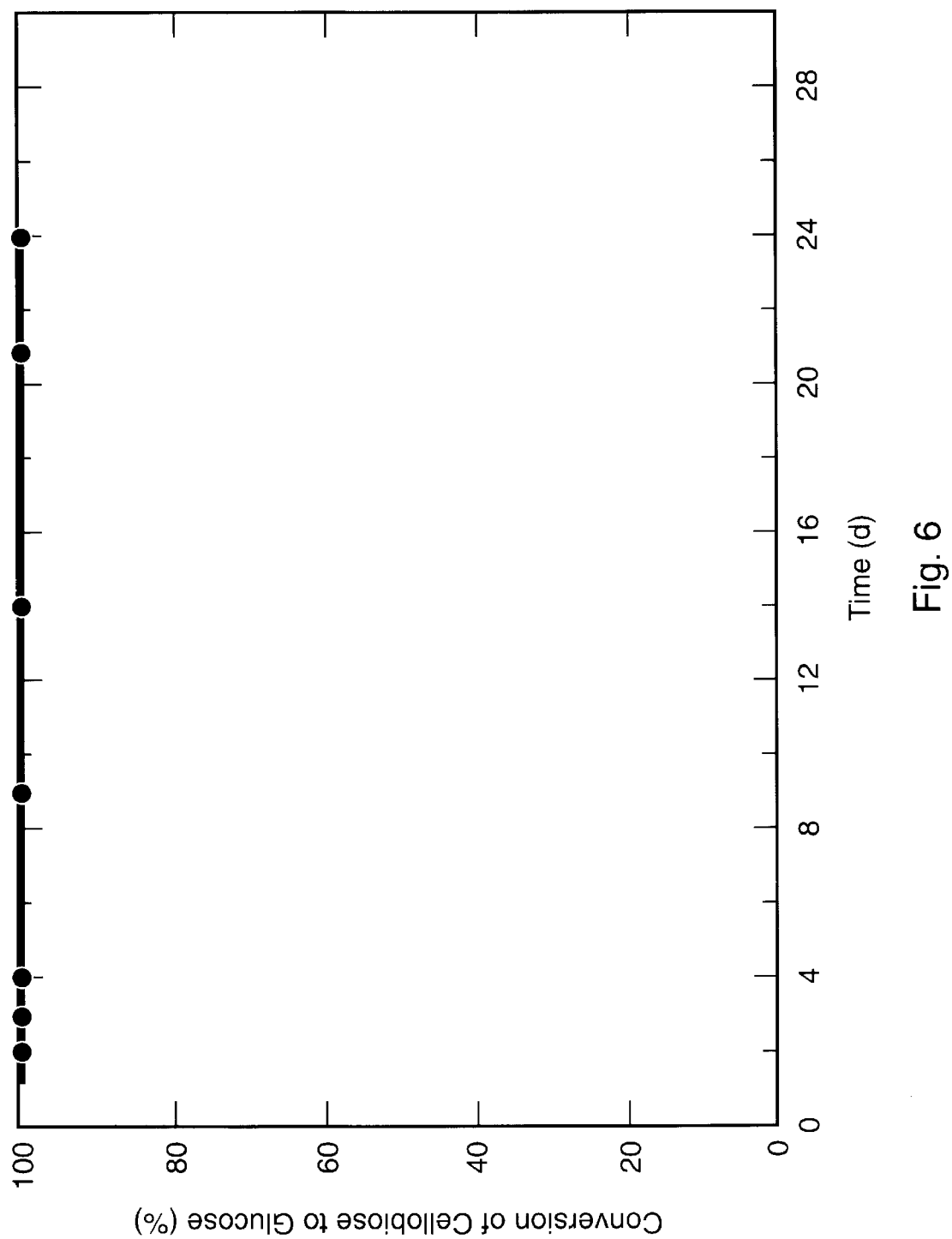

STRUCTURALLY STABLE GEL BEAD CONTAINING ENTRAPPED ENZYME AND METHOD FOR MANUFACTURE THEREOF

This application is a continuation of application Ser. No. 07/936,162, filed Aug. 26, 1992, now abandoned.

This invention was made with Government support under Contract No. DE-AC05-OR21400 awarded by the Office of Basic Energy Sciences, Chemical Sciences Division, of the U.S. Department of Energy to Martin Marietta Energy Systems, Inc. and the Government has certain rights in the invention.

FIELD OF THE INVENTION

This invention relates to the immobilization of enzymes, and more particularly to a structurally stable gel bead containing a covalently bound enzyme and a method for manufacture thereof.

BACKGROUND OF THE INVENTION

The immobilization of enzymes has included several approaches, among them are physical adsorption, carrier-binding, cross-linking, and entrapping. Physical adsorption relies on the support having an affinity for the enzyme. This method of immobilization can be very weak and the enzyme can readily be desorbed and lost. Carrier-binding involves connecting the enzyme to a water-insoluble support by ionic or covalent bonds. Cross-linking is performed by making chemical bridges or connections between and within molecules. These bridges, or cross-links, insolubilize the enzyme by creating large molecular aggregates. These cross-links also impart rigidity and physical strength to the enzyme. Entrapping is accomplished by enclosing the enzyme within a suitable material. The openings in the encapsulating material have to be of sufficient size to permit the substrate or reactant to pass through to the enzyme without allowing the enzyme to leak out. It is also possible to combine these various methods in a number of configurations.

Cellobiase, also referred to as β-glucosidase, catalyzes the hydrolysis of cellobiose, a dimer of glucose, into glucose. Cellobiase is a vital component of the complex mixture of enzymes termed cellulase that catalyze the hydrolysis of cellulose to glucose. Cellobiase catalyzes the hydrolysis the β(1,4) bond in cellobiose, yielding two molecules of glucose. Without cellobiase being present in sufficient quantity, little glucose is formed. The main product of this cellulose hydrolysis reaction is cellobiose which, in turn, inhibits the reaction so that cellulose hydrolysis is greatly impaired. The process chemistry of interest is listed below:

Over-all Hydrolysis of Cellulose to Glucose (1)

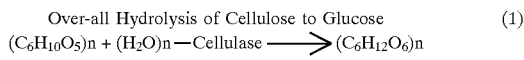

cellulose    water    enzyme    glucose

Cellobiose Formation (an inhibiting intermediate product) (2)

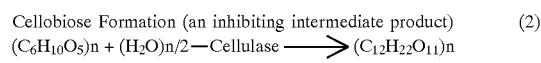

cellulose    water    enzyme    cellobiose

Hydrolysis of Cellobiose to Glucose (3)

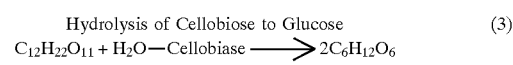

cellulose    water enzyme    glucose

The supplementation of commercially produced cellulases with cellobiase, such as that produced by the fungus *Aspergillus niger*, increases the rate and extent of glucose production. The level of cellobiase activity in cellulase is, therefore, insufficient for the maximum rate and extent of glucose production that is preferred.

Since the substrate of cellobiase, cellobiose, is water soluble, an immobilized (water insoluble) cellobiase preparation could be used to supplement commercial cellulase/cellulose mixtures, and such a preparation could be subsequently recovered and reused. Previously, it was observed that cellobiase, normally inhibited by cellobiose concentrations greater than 10 mM, was not subject to inhibition by cellobiose concentrations as high as 100 mM, if the cellobiase was immobilized and entrapped within calcium alginate gel beads. However, the disadvantage of using calcium alginate gel beads is that they are not structurally stable in continuous flow systems unless calcium ions are added.

The development of maintenance-free propylene glycol alginate/bone gelatin gel beads for the entrapment of microorganisms eliminated this disadvantage. A complete description of this technology is found in U.S. Pat. Nos. 4,978,647 and 4,995,985, both to Scott et al., the entire disclosures of both of which are incorporated herein by reference. These gel beads are generally made structurally stable by soaking them in 0.1N sodium hydroxide (NaOH) for at least 15 minutes and after such treatment require no further maintenance (i.e., addition of metal ions). However, storage in the NaOH solution even for a few minutes, when used for entrapment of an enzyme, results in a dramatic decline in enzyme activity due to alkali inactivation. Storage in an alkali solution, such as NaOH, for less time generally results in the formation of unstable gel beads.

There is a need for a gel bead containing an entrapped enzyme that: (1) will not leak the enzyme from the gel bead, (2) is structurally stable without the use of additives, and (3) can be used for the continuous hydrolysis of various substrates in a variety of different bioreactor configurations for enhancing the rate and extent of the enzymatic alteration of those substrates.

OBJECTS OF THE INVENTION

Accordingly, it is an object of the present invention to provide a new and improved method of immobilizing enzymes.

It is another object of the present invention to provide a new and improved method of increasing the useful life of immobilized enzymes.

It is another object of the present invention to provide a new and improved method for enzymatic reactions.

It is another object of the present invention to provide a new and improved gel bead containing immobilized enzymes.

Further and other objects of the present invention will become apparent from the description contained herein.

SUMMARY OF THE INVENTION

In accordance with one aspect of the present invention, the foregoing and other objects are achieved by:

A structurally stable gel bead containing an entrapped enzyme, said gel bead being comprised of gelatin, said enzyme being covalently cross-linked to said gelatin.

In accordance with another object of the present invention, the foregoing and other objects are achieved by:

mixing an enzyme with gelatin to form a mixture;

adding glutaraldehyde to the mixture so that the enzyme covalently cross-links to the gelatin;

forming a gel bead from the mixture;

soaking the gel bead in glutaraldehyde for a sufficient period of time to impart structural stability to the gel bead; and recovering the gel bead.

In accordance with another object of the present invention, the foregoing and other objects are achieved by:

providing structurally stable gel beads containing an entrapped enzyme, said gel beads being comprised of gelatin, said enzyme being covalently cross-linked to said gelatin;

contacting a substrate with said gel beads to produce a product; and recovering said product.

BRIEF DESCRIPTION OF THE DRAWINGS

FIG. 6 is a graphical illustration of the conversion of cellobiose to glucose by the cellobiase entrapped gel beads in a continuous-flow bioreactor as a function of time, in accordance with the present invention.

DETAILED DESCRIPTION OF THE PREFERRED EMBODIMENT

Figure 1:
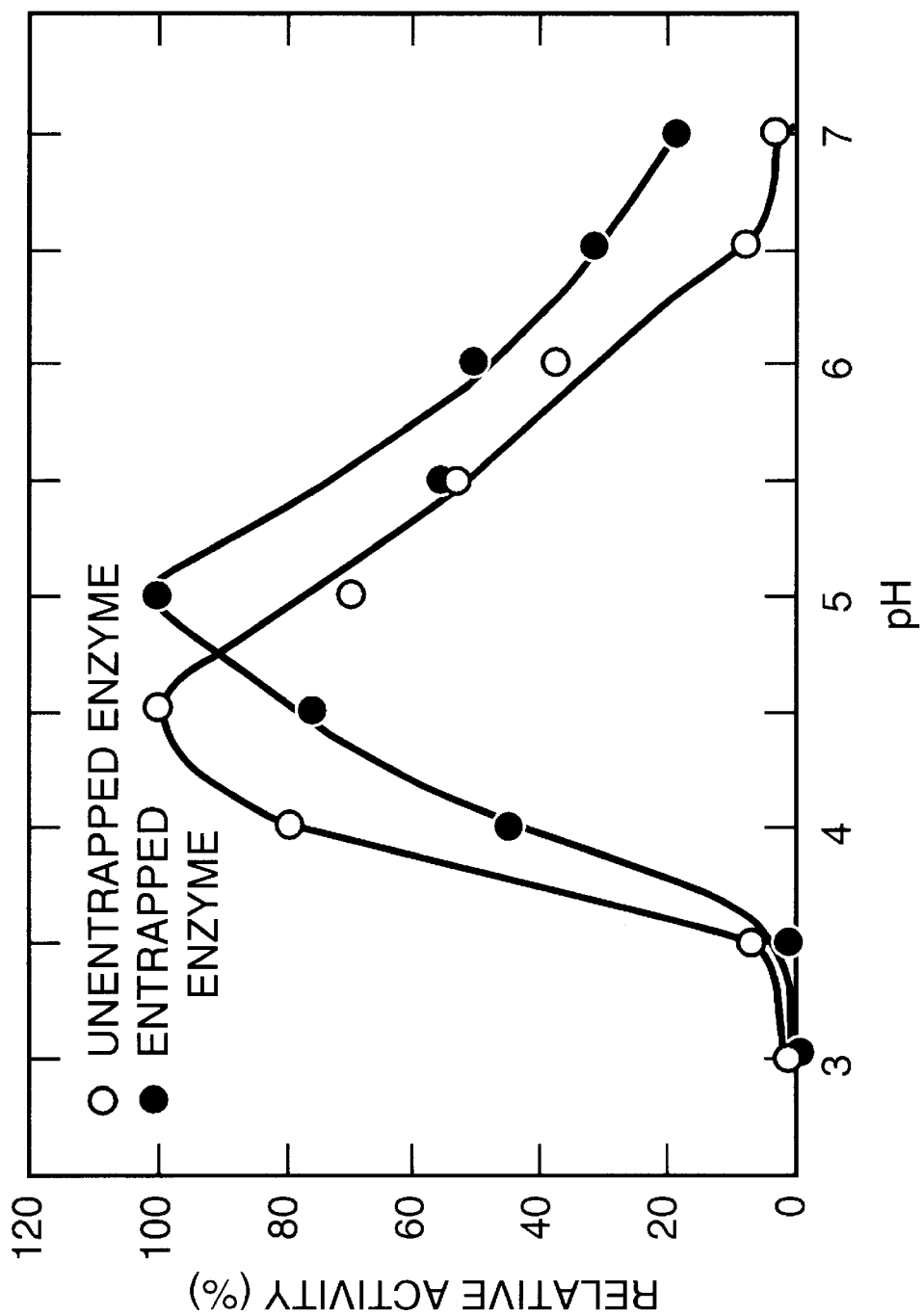
FIG. 1 is a graphical illustration of the effect of pH on cellobiase activity of the gel beads, prepared in accordance with the present invention.

One embodiment of the present invention involves the covalent bonding, via cross-linking in the presence of glutaraldehyde, of cellobiase to gelatin prior to the formation of the gel bead which prevents leakage of the cellobiase. Additionally, propylene glycol alginate is added prior to gel bead formation to enhance structural stability. Once the gel beads are formed, structural stabilization of the gel beads is subsequently achieved by soaking them in a glutaraldehyde solution. The resulting gel beads are structurally stable for an extended period, during which time the catalytic activity of cellobiase does not decline to any significant extent. These gel beads can be used for the continuous hydrolysis of cellobiose to glucose, as well as other enzymatic processes.

Cellobiase was obtained from Novo Nordisk Bioindustrials, Inc., Danbury, Conn. The product is named Novozym 188 by its manufacturer and is produced by submerged fermentation of a selected strain of *Aspergillus niger*. Deionized bone gelatin was obtained from Rousselot, Paris, France. Propylene glycol alginate (Kelcoloid S) was purchased from Kelco, Clark, N.J. Cellobiose and glutaraldehyde (25% weight/volume (w/v) grade I) were purchased from Sigma Chemical Company, St. Louis, Mo. Disposable PD-10 columns containing Sephadex G-25M gel were purchased from Pharmacia, Piscataway, N.J. An example of a cellobiase entrapped gel bead and a method for its manufacture, in accordance with one aspect of the present invention, is presented below:

Example I

A solution containing cellobiase (1–10% volume/volume (v/v)) and cellobiose (0.26% w/v) cellobiose was mixed with an amount of bone gelatin (final concentration 1% w/v) in 50 mM sodium acetate at pH 5.0. The sodium acetate solution acts as a buffer, ensuring that the proper pH level is maintained. The cellobiose was added to protect the enzyme's catalytic site from any possible inactivation by glutaraldehyde. Glutaraldehyde was added to a final concentration of 0.5% (v/v). The solution was then allowed to incubate for 1 hour at 23° C. so that the cellobiase covalently cross-linked with the gelatin. The solution was then dialyzed at 4° C. for 18 hours to remove the excess glutaraldehyde and essentially all of the cellobiose. The solution was then placed in a mixing apparatus, wherein propylene glycol alginate (2% w/v final concentration) was added. This mixture was stirred at 40° C. for 15–30 minutes until everything was dissolved, resulting in the formation of a viscous solution. The viscous solution was then transferred to a gel bead production apparatus and kept at 40° C. Gel beads were formed by using 20 lbs/in. of gas pressure (helium or nitrogen) to force the viscous liquid through the needle as discrete droplets which fell into 500 mL of mineral oil on the surface of 200 mL of ice cold 50 mM sodium acetate at pH 5.0. The gel beads were removed from the oil/aqueous interface and stored for 20 hours at 4° C. in a 0.5% (w/v) solution of glutaraldehyde at pH 5.0. They were then washed with 4×500 mL of distilled water and 3×200 mL of 50 mM sodium acetate at pH 5.0, and stored in the sodium acetate solution at pH 5.0.

Example II describes a test of a cellobiase entrapped gel bead and a method for its manufacture, in accordance with one aspect of the present invention:

Example II

The cellobiase was prepared as follows: 1 mL of the crude cellobiase was mixed with 4.0 mL of a solution of 50 mM sodium acetate at pH 5.0. The sodium acetate solution acts as a buffer, ensuring that the proper pH level is maintained. The cellobiose was added to protect the enzyme's catalytic site from any possible inactivation by glutaraldehyde. Two aliquots, each consisting of 2.5 mL of this solution, were then filtered through a PD-10 column, and the filtered cellobiase (total volume 7.0 mL) was used for gel entrapment as described below. One gram of bone gelatin and 0.2567 grams of cellobiose were dissolved in 44 mL of a solution of 50 mM sodium acetate at pH 5.0. The final cellobiose concentration was 15 mM. One mL of glutaraldehyde and 5.0 mL of the filtered cellobiase were added to this solution, and the mixture was incubated at 23° C. for 1 hour. This was done to covalently cross-link the cellobiase, a protein, to gelatin, which is also a protein. The solution was then dialyzed at 4° C. for 20 hours to remove excess glutaraldehyde and essentially all of the cellobiose. 25 mL of the dialyzed solution was then placed in a mixing apparatus. The activity of the filtered cellobiase was determined to be approximately 170 units/mL, where 1 unit is defined as that amount of enzyme required to produce 1 $\mu$mol glucose/minute from 10 mM cellobiose at 40° C. in 50 mM sodium acetate at pH 5.0. Two grams of propylene glycol alginate, 14.5 grams of bone gelatin, and 75 mL of 50 mM sodium acetate at pH 5.0 were added to the mixture. The 2% (w/v)

propylene glycol alginate used in the manufacture of the gel beads is important for maintaining structural integrity prior to their being soaked in glutaraldehyde. Propylene glycol alginate and bone gelatin are not inhibitors of cellobiase activity. The mixture was stirred at 40° C. for 15–30 minutes until everything was dissolved, resulting in the formation of a viscous solution. The viscous solution was then transferred to a gel bead production apparatus and kept at 40° C. Gel beads were formed by using 20 lbs/in. of gas pressure (helium or nitrogen) to force the viscous liquid through the needle as discrete droplets which fell into 500 mL of mineral oil on the surface of 200 mL of ice cold 50 mM sodium acetate at pH 5.0. One hundred mL of gel beads, 2 mm in diameter were formed. The gel beads were removed from the oil/aqueous interface and stored for 20 hours at 4° C. in a 0.5% (w/v) solution of glutaraldehyde at pH 5.0. They were then washed with 4×500 mL of distilled water and 3×200 mL of 50 mM sodium acetate at pH 5.0, and stored in the sodium acetate solution at pH 5.0. Enzymatic activity was monitored during the procedures involved in the entrapment of cellobiase within the gel beads, and the results are shown in Table 1.

TABLE 1*

| Initial Activity | Activity After Cross-Linking | Activity in Supernatant | Entrapped Activity |
|---|---|---|---|
| 877 | 790 | 0 | 238 |

*Values refer to total activity (i.e. 100 mL of gel beads contained 238 units of cellobiase activity).

Table 1 indicates that after covalently cross-linking cellobiase to gelatin, followed by dialysis, there was only a 10% loss in activity. There was a negligible loss in activity from the gel beads into the sodium acetate solution (supernatant) after gel bead formation. The total activity of the gel beads represented 27% of the original activity. This is only an apparent loss in activity, and may possibly be caused by substrate diffusion and/or by the soaking time of the gel beads in the glutaraldehyde solution.

It should be noted that the initial amount of cellobiase that can be covalently cross-linked to the gelatin can be increased to as much as 50 mL of the filtered cellobiase solution. Consequently, the amount of entrapped cellobiase can be varied. Additionally, the soaking time of the gel beads in the glutaraldehyde solution can be varied according to the temperature of the glutaraldehyde solution. For example, the soaking time may only be one hour if the glutaraldehyde solution is at room temperature. This parameter, soaking time, is not critical to the overall performance of the gel beads, provided that the gel beads are soaked in the glutaraldehyde for a sufficient period of time to impart structural stability to the gel beads.

The pH activity profile of the entrapped enzyme was shifted slightly more towards the alkaline side (FIG. 1); the pH optimum of the unentrapped and entrapped enzyme being 4.5 and 5.0, respectively. The reason for this may probably be related to unequal distribution of hydrogen and hydroxyl ions between the gelatin (to which cellobiase is attached), making up the bulk of the gel bead, and the external solution. The preferred pH range of the entrapped cellobiase is about 4 to about 6, with a functional pH range of about 3 to about 7.

Figure 2:
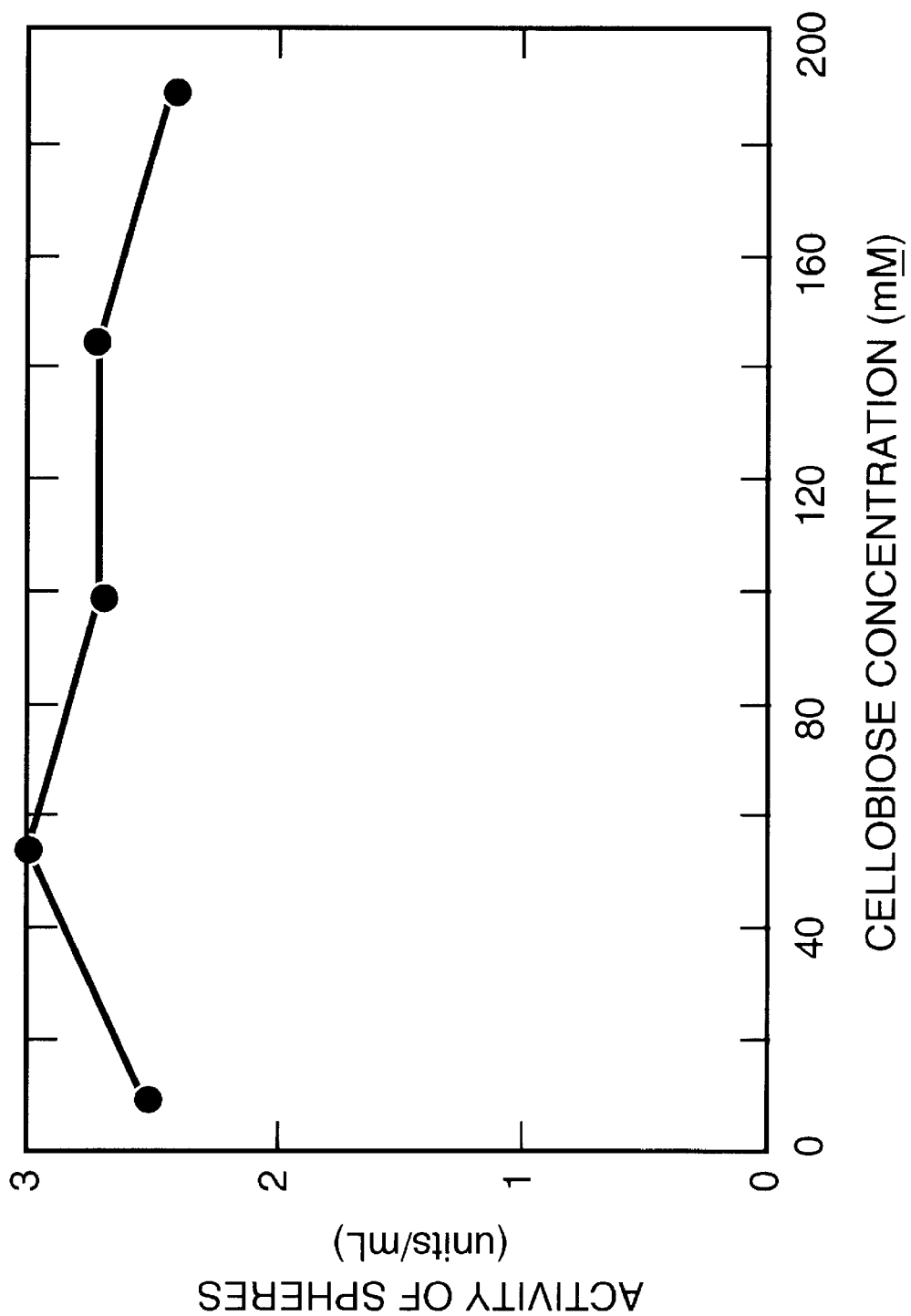
FIG. 2 is a graphical illustration of the effect of cellobiose concentration on the cellobiase activity of the gel beads, prepared in accordance with the present invention.

It has been previously reported that gel bead-entrapped cellobiase is not subject to substrate inhibition unlike unentrapped cellobiase. This was also found to be the case for cellobiase entrapped within the subject gel beads (FIG. 2).

The cellobiase activity of the gel beads (~2.5 units/mL gel bead) of the present invention was virtually unchanged between a substrate (cellobiose) concentration of 10–190 mM (0.342–6.5% (w/v)).

Figure 3:
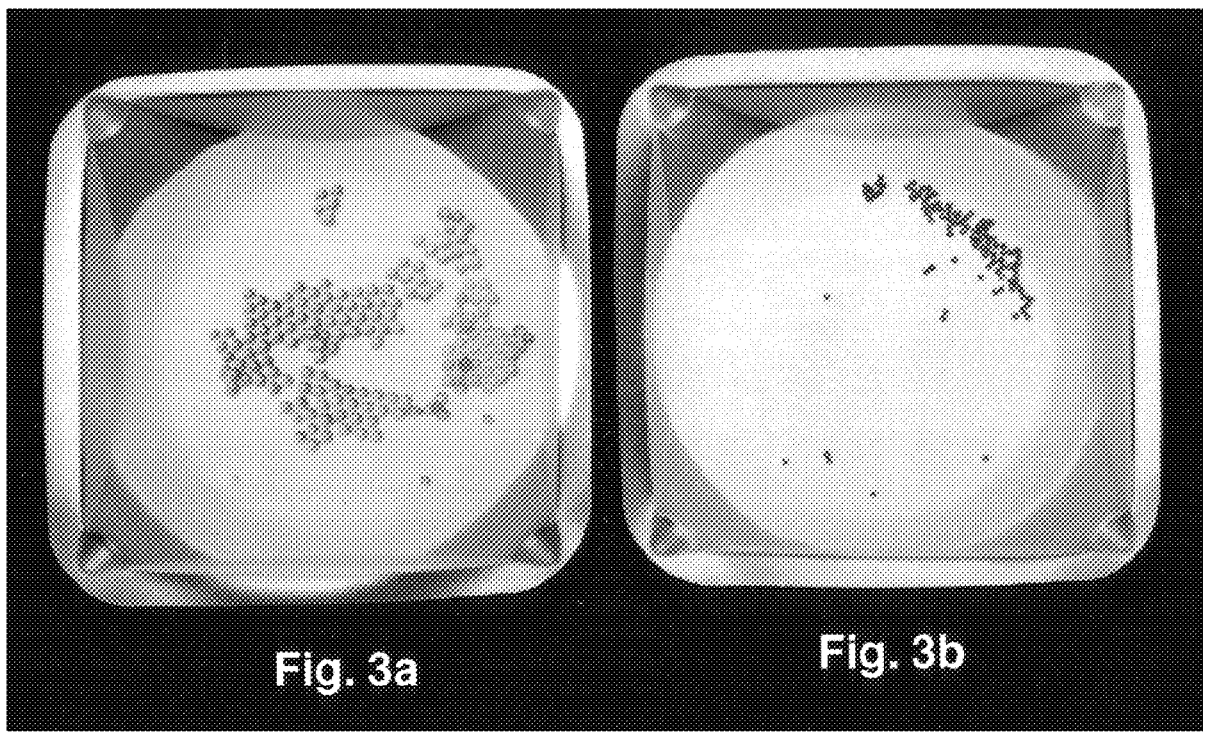
FIG. 3a is a photographic illustration of hydrated gel beads, prepared in accordance with the present invention.
FIG. 3b is a photographic illustration of dehydrated gel beads, prepared in accordance with the present invention.

The hydrated gel beads, as shown in FIG. 3A, were 2 mm in diameter and could be dried in air at 23° C., resulting in hard pellets that were 1 mm in diameter (FIG. 3B). It is important to note that these gel beads can be dehydrated and rehydrated repeatedly. This is in contrast to calcium alginate and kappa-carrageenan gel beads which, once dehydrated, generally cannot be rehydrated. The gel beads of the present invention were dehydrated/rehydrated 5 times with approximately 20% loss in initial gel bead activity. Rehydration of these gel beads was accomplished by soaking them in 50 mM sodium acetate at pH 5.0, for 30 minutes. The shelf-life of these gel beads and the cellobiase activity within them can probably be measured in years. The dehydrated gel beads are not hygroscopic when exposed to a climate controlled environment.

Figure 4:
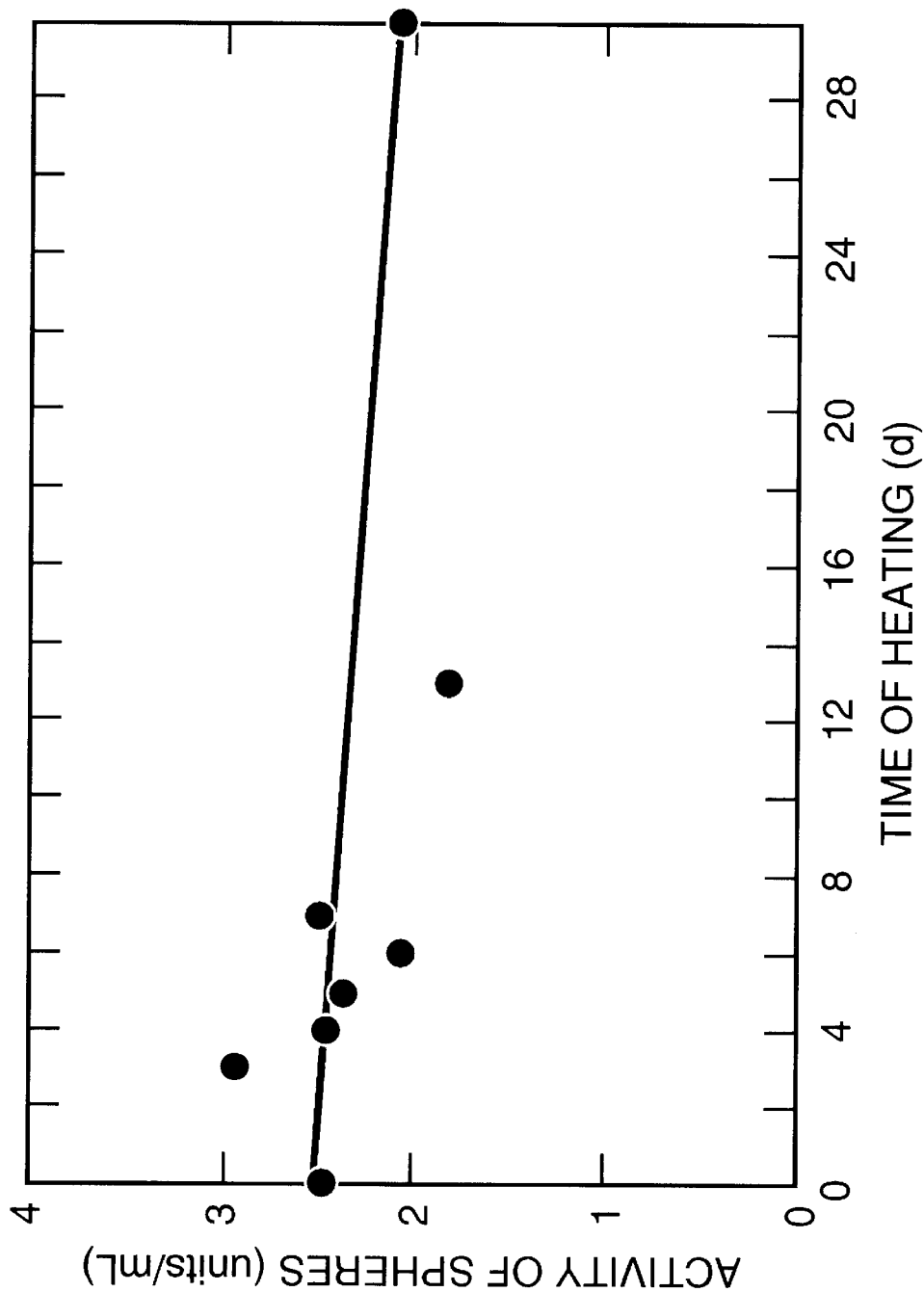
FIG. 4 is a graphical illustration of the thermal stability at 40° C. of the cellobiase entrapped gel beads, prepared in accordance with the present invention.

The gel beads containing entrapped cellobiase were stirred at 40° C. in 50 mM sodium acetate at pH 5.0, and 0.1% sodium azide as a preservative/bacterial growth inhibitor. There was little loss in activity after 30 days (FIG. 4) and the activity has been shown to be stable for up to 200 days at this temperature. The catalytic activity of the gel beads is very stable under these conditions. Additionally, there is not any significant leakage of cellobiase from the gel beads during this time; otherwise, the activity of the gel beads would have been expected to decline. No significant enzymatic activity was measured in the solution in which the gel beads were stirred indicating that enzyme leakage did not occur.

Figure 5:
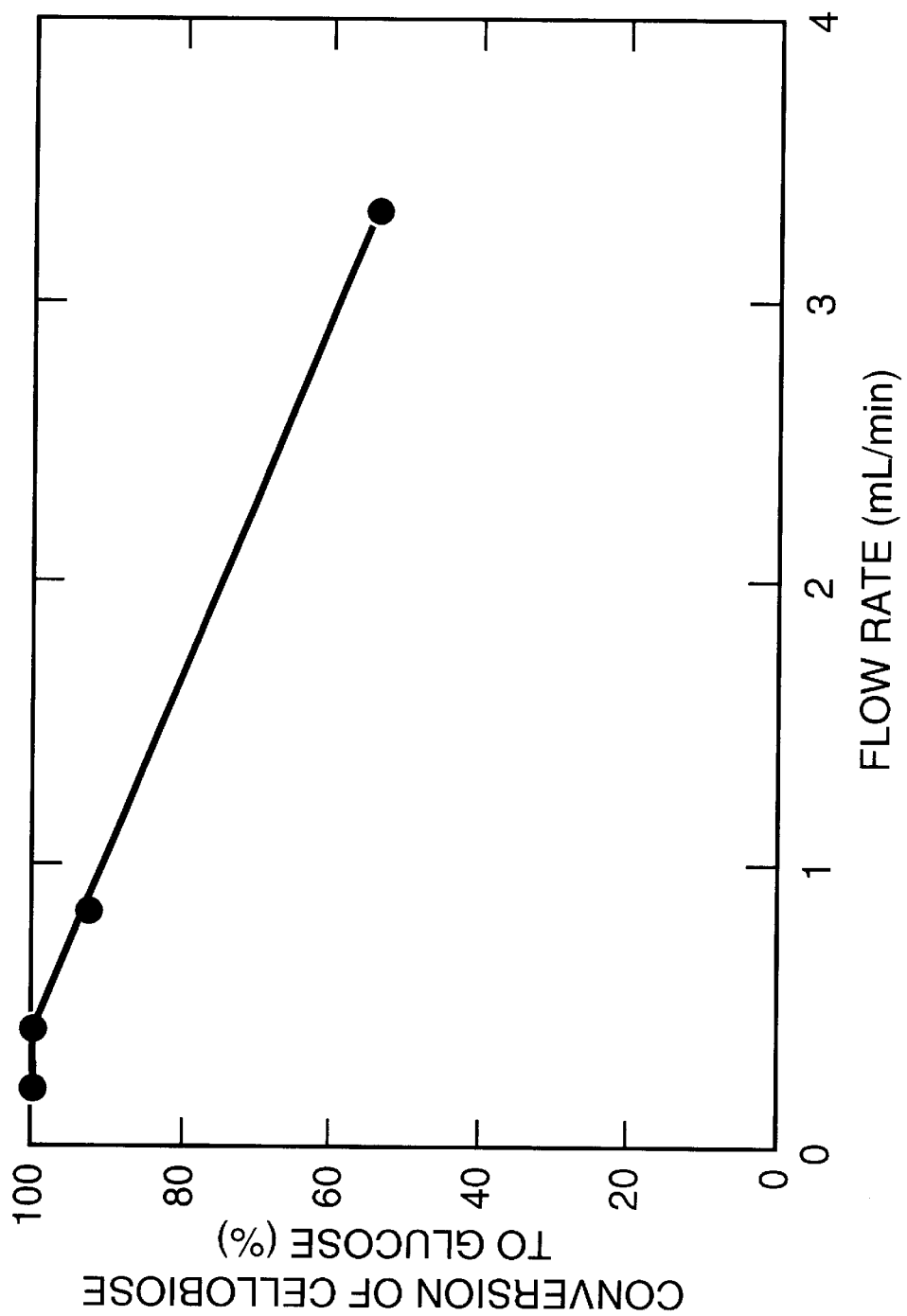
FIG. 5 is a graphical illustration of the effect of flow rate on the conversion of cellobiose to glucose by the cellobiase entrapped gel beads in a continuous-flow bioreactor, in accordance with the present invention.

An example of a bioreactor utilizing cellobiase entrapped gel beads for the conversion of cellobiose to glucose, in accordance with one aspect of the present invention, is presented below:

Example III 33 mL of gel beads containing entrapped cellobiase (~80 units of activity) were packed in a thermojacketed tapered bioreactor at 40° C., total volume 50 mL. A solution of cellobiose (10 mM or 0.342% (w/v) in 50 mM sodium acetate at pH 5.0, containing 0.1% sodium azide) was pumped upwardly through the column at different flow rates. The glucose concentration of the effluent was then determined. The effect of the flow rate on the percent conversion of cellobiose to glucose is shown in FIG. 5. There was a 100% conversion of cellobiose to glucose at a flow rate of 0.2 mL/min which was maintained over a period of 200 days (FIG. 6). This indicates that the gel beads containing entrapped cellobiase are catalytically stable, and do not lose their catalytic activity through leakage.

Although directed primarily towards to the entrapment of cellobiase in propylene glycol alginate/bone gelatin gel beads, the present invention may be practiced with many different types of enzymes, such as (but not limited to) proteases, carbohydrases, lipases, ligases (synthetases), isomerases, oxidoreductases, and specialty enzymes. Proteases are generally defined as those enzymes that catalyze the hydrolysis of peptide bonds in proteins. Carbohydrases are generally defined as those enzymes that catalyze the hydrolysis of disaccharides and more complex carbohydrates. Lipases are generally defined as those enzymes that catalyze the hydrolysis of the ester bonds in fats and oils. Ligases are generally defined as those enzymes that catalyze the union of two molecules. Isomerases are generally defined as those enzymes that catalyze isomer conversion reactions. Oxidoreductases are generally defined as those enzymes that catalyze the reduction or oxidation of molecules. Certain proteases, such as trypsin or pepsin can be used to break down proteins and polypeptides. Amylase can be used for the production of fermentable sugars from starch. Glucoamylase can be used for the continuous hydrolysis of soluble dextrins (glucose polysaccharide chains) of a high molecular size that can allow their diffusion into the interior of the gel beads. Glucose isomerase can be used for the production of high fructose corn syrup (a mixture of glucose and fructose). β-Galactosidase can be used for lactose removal from dairy products. Lipases can be immobilized and used for the manufacture of sugar esters and high value oils. Thermolysin can be used for the production of aspartame. Glucose oxidase can be used for the generation of gluconic acid, as a glucose bioreagent, as well as for the removal of oxygen. Penicillin acylase can be used for the manufacture of semisynthetic antibiotics from penicillin. Urease can be used for the removal of urea from blood and/or plasma. These and other enzymes can immobilized in the gel beads of the present invention and utilized in a number of configurations for various enzymatic processes. A minimal amount of experimentation is expected of one skilled in the art to determine which enzymes are most suitable.

While there has been shown and described what are at presented considered the preferred embodiments of the invention, it will be obvious to those skilled in the art that various changes and modifications can be made therein without departing from the scope of the invention defined by the appended claims.

What is claimed is:

1. A structurally stable gel bead containing an entrapped enzyme, said structurally stable gel bead containing an entrapped enzyme being comprised of gelatin and propylene glycol alginate, said propylene glycol alginate being present in a final concentration of about 2% weight/volume, said enzyme being maintained at a pH in the range of 3 to less than 7, said enzyme being covalently cross-linked to said gelatin, said structurally stable gel bead containing an entrapped enzyme being capable of being dehydrated and rehydrated, said enzyme being selected from the group consisting of proteases, carbohydrases, lipases, isomerases, ligases, and oxidoreductases.

2. A method of entrapping an enzyme within a gel bead comprising the steps of:

mixing an enzyme with gelatin to form a mixture, said enzyme being maintained at a pH in the range of 3 to less than 7, said enzyme being selected from the group consisting of proteases, carbohydrases, lipases, isomerases, ligases, and oxidoreductases;

adding glutaraldehyde to the mixture so that the enzyme covalently cross-links to the gelatin;

adding propylene glycol alginate to the mixture, said propylene glycol alginate being present in a final concentration of about 2% weight/volume;

forming a gel bead from the mixture;

soaking the gel bead in glutaraldehyde for a sufficient period of time to impart structural stability to the gel bead; and recovering the gel bead, said gel bead being capable of being dehydrated and rehydrated.

3. An enzymatic process comprising the steps of:

providing structurally stable gel beads containing an entrapped enzyme, said structurally stable gel beads containing an entrapped enzyme being comprised of gelatin and propylene glycol alginate, said propylene glycol alginate being present in a final concentration of about 2% weight/volume, said enzyme being covalently cross-linked to said gelatin, said enzyme being maintained at a pH in the range of 3 to less than 7, said structurally stable gel beads containing an entrapped enzyme being capable of being dehydrated and rehydrated, said enzyme being selected from the group consisting of proteases, carbohydrases, lipases, isomerases, ligases, and oxidoreductases;

contacting a substrate with said gel beads to produce a product; and recovering said product.

* * * * *